United States Patent [19]
Kostich

[11] Patent Number: 4,622,185
[45] Date of Patent: Nov. 11, 1986

[54] METHOD AND APPARATUS FOR MOLDING AND ACCURATELY REPOSITIONING SELECTED PORTIONS OF THE HUMAN ANATOMY

[75] Inventor: Jeffrey V. Kostich, Akron, Ohio

[73] Assignee: Smithers Medical Products, Inc., Hudson, Ohio

[21] Appl. No.: 723,146

[22] Filed: Apr. 15, 1985

[51] Int. Cl.[4] .................. B28B 7/34; B29C 67/22; B29C 33/40
[52] U.S. Cl. .................. 264/45.2; 249/65; 249/203; 264/222; 264/314; 264/DIG. 29
[58] Field of Search ............ 264/222, 45.2, 223, 264/314; 425/DIG. 29; 249/65, 203

[56] References Cited

U.S. PATENT DOCUMENTS

| | | | |
|---|---|---|---|
| 3,048,169 | 8/1962 | Pierce | 264/222 X |
| 3,403,676 | 10/1968 | Gibbons | 264/45.2 X |
| 4,327,046 | 4/1982 | Davis et al. | 264/222 X |
| 4,347,213 | 8/1982 | Rogers, Jr. | 264/222 X |
| 4,450,122 | 5/1984 | Gallina | 264/223 X |

OTHER PUBLICATIONS

Hall, B. P. and D. A. Moore, "Blown Polyurethane Medical Casts" in *IBM Technical Disclosure Bulletin,* vol. 12, No. 4, Sep. 1969, p. 535.

*Primary Examiner*—Philip Anderson
*Attorney, Agent, or Firm*—Renner, Kenner, Greive, Bobak & Taylor

[57] ABSTRACT

The base (11) of a template forming device (10) has a planar, upper surface (12) onto which a plurality of orthogonal grooves (14 and 15) are recessed. A foam mixture is introduced into a container means (20) received on the base (11), and a plurality of restraining means in the form of slats (18) are insertably received within selected grooves (14 and 15) to confine the foaming action within the container means (20) and to direct it against a selected portion of the anatomy so that when the foam is fully risen and cured a template (40) is provided which can be repeatedly used accurately to reposition and support that portion of the patient's anatomy.

12 Claims, 7 Drawing Figures

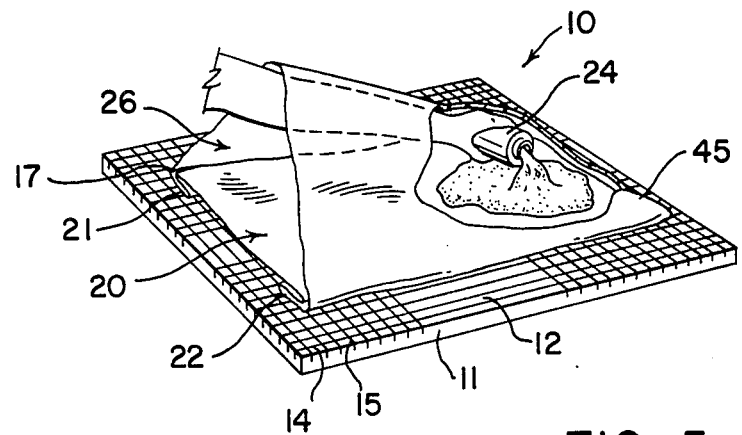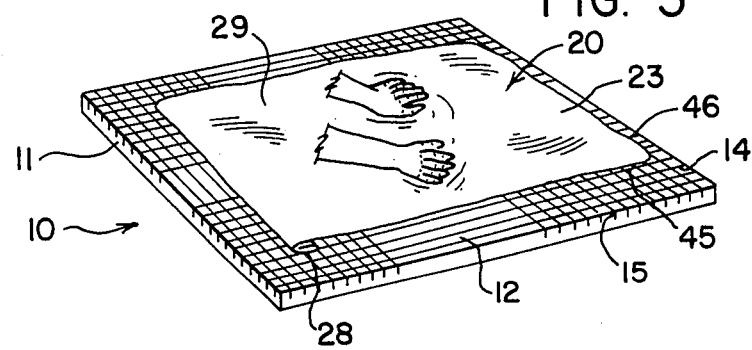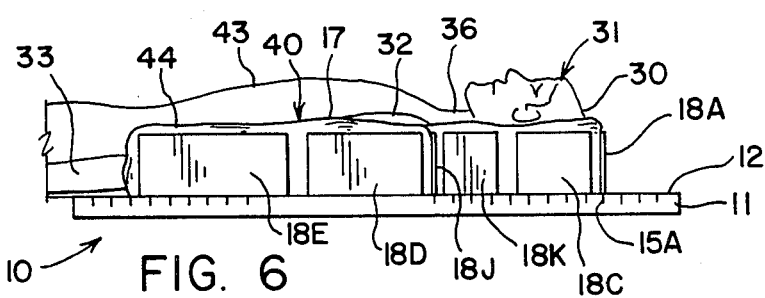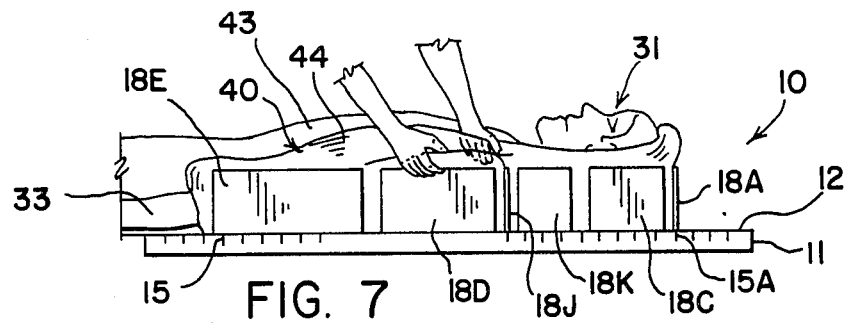

METHOD AND APPARATUS FOR MOLDING AND ACCURATELY REPOSITIONING SELECTED PORTIONS OF THE HUMAN ANATOMY

TECHNICAL FIELD

The present invention relates generally to a method and apparatus that is particularly adapted to be utilized by doctors, hospitals and related medical facilities. More particularly, the present invention relates to a method and apparatus by which to mold a permanent impression, or template, of a selected portion of a patient's anatomy and thereafter be able to employ that impression exactly to reposition that same selected portion of the patient's anatomy. Specifically, the present invention relates to a method and apparatus by which a foam mixture can be directed and selectively molded to conform to any desired portion of the human anatomy whereby to make a permanent impression thereof that can subsequently, and repeatedly, be employed as a template accurately to reposition that same portion of the anatomy from which the template was originally molded and thereby to support that portion of the patient's anatomy in such a way as to assist the patient in maintaining the supported portion of the anatomy virtually motionless.

BACKGROUND ART

The efficiency and effectiveness of certain medical procedures can be considerably enhanced if that portion, or those portions, of the patient's anatomy requiring treatment can be quickly and accurately positioned and comfortably supported during successive treatments. This need to be able accurately to position, and successively reposition, a portion of the patient's anatomy and then maintain it virtually motionless is exemplified by considering a series of radiation treatments. The radiation beam must be projected to an exact location, sometimes interiorly of the body. Such a radiation beam must be most accurate in order not to inflict damage to the tissues surrounding the area to be treated, and as a result there is little margin for error. Not only must the radiation beam be projected accurately toward a particular spot on the body surface, the body must also be precisely oriented to effect the required alignment of the radiation beam from the surface of the body to the interiorly located tissue being treated. Moreover, once the patient is positioned and aligned he, or she, must remain as reasonably motionless as possible. Radiation treatment generally requires repeated exposures over a period of several weeks. Thus, the difficulties are compounded without a template by which quickly and accurately to reposition and support the patient during successive treatments in exactly the same position initially determined.

One approach for making such a template has been to create a lasting impression by allowing foam simply to rise up around the patient and to cure as it has so risen. However, this results in a relatively poor template inasmuch as the foam often does not accurately conform to the side contours of the patient's anatomy.

A more sophisticated attempt has been to use mass produced forms which approximate selected portions of the human anatomy. A foam is poured into the form, the patient is specifically positioned within the form, and the foam rises around the contours of the patient and is restricted by the walls of the form.

Practical considerations permit such forms to be provided in only two sizes—pediatric and adult—but there is no other reasonable means by which to personalize the forms to the size of the various patients to be treated. Because of the sheer bulk of the individual forms, and the number of different forms required to accommodate the several portions of the anatomy for which a template might be needed it is not practical to make, and stock, each form in a plurality of sizes. But even if one had the vast storage space available to stock all the various forms in a wide variety of sizes, true customizing of the template to the exact parameters desired for all patients would still not be readily feasible.

DISCLOSURE OF THE INVENTION

It is, therefore, a primary object of the present invention to provide an improved method and apparatus by which to mold a template to selected portions of the human anatomy, which template can be repeatedly employed quickly and accurately to reposition those selected portions of the patient's anatomy in the exact position initially selected.

It is another object of the present invention to provide a method and apparatus, as above, by which the template can be personalized to any patient, irrespective of the portion of the anatomy involved, or the size of the patient.

It is a further object of the present invention to provide an improved method and apparatus, as above, by which to direct and maintain the foam against selected portions of a patient's anatomy until the foam has fully cured.

It is an even further object of the present invention to provide a method and apparatus, as above, that utilizes a homogeneous foam mixture from which to mold the desired template.

It is yet another object of the present invention to provide an apparatus, as above, which is of relatively simple configuration, which is economical to make and use, which requires relatively little space to store, which can be effectively employed with only moderate practice and skill and which need be provided in only one size to accommodate all patients.

These and other objects of the invention, as well as the advantages thereof over existing and prior art forms, will be apparent in view of the following detailed description of the attached drawings and are accomplished by means hereinafter described and claimed.

In general, an apparatus embodying the concept of the present invention employs a relatively rigid base. A plurality of orthogonally disposed grooves, or slots, are recessed into the base, and a flexible container overlies at least a portion of said base. To use this apparatus a foaming mixture is introduced into the flexible container means, and it is distributed as evenly as possible within the container means. As soon as the foam begins to rise, that portion of the patient's anatomy for which a template is to be molded is disposed in the desired position upon the flexible container. As the foam rises a plurality of slat means are insertably received within the grooves in the base to direct and maintain the container, with the foam forming therein, in contiguous juxtaposition with at least the lower and side contours of that portion of the patient's anatomy for which a template is to be molded.

When the foam sets, the slat means are removed, the patient is extricated from the now relatively firm, foam filled container—which constitutes the template—and the thus formed template may be removed from the base for final curing.

At any time that the appropriate portion of the patient's anatomy is to be repositioned, it is reinserted within the template, and the template is positioned on the treatment bench disposed in conformity with the disposition of the base when the template was formed. In that way the desired portion of the patient's anatomy is not only disposed exactly as it was when the template was originally formed but it is also restfully supported so that the patient need merely relax and permit the template to effect the desired support.

BRIEF DESCRIPTION OF THE DRAWINGS

FIG. 4 is a schematic perspective similar to that of FIG. 1, but of reduced scale and depicting the introduction of the mixed, foam forming chemicals into the container means;

FIG. 5 is a schematic representation similar to that of FIG. 5 and depicting the container means closed and the hands of the technician using the device spreading the chemicals within the folded container means and smoothing the surface thereof;

FIG. 6 is a schematic side elevation of the device depicted in FIGS. 5 and 6, but depicting the next sequential step in the use of the exemplary device following the step depicted in FIG. 5—i.e., the pertinent portion of the patient's anatomy having been selectively received within the appropriate slots to maintain the container in which the foam is rising in conforming juxtaposition with the contour of the patient's anatomy for which a template is to be molded.

FIG. 7 is a schematic side elevation similar to that depicted in FIG. 6 with portions of the sides of the container being unfolded selectively to increase the degree to which desired portions of the patient's anatomy are encapsulated.

EXEMPLARY EMBODIMENT OF THE INVENTION

Figure 1:
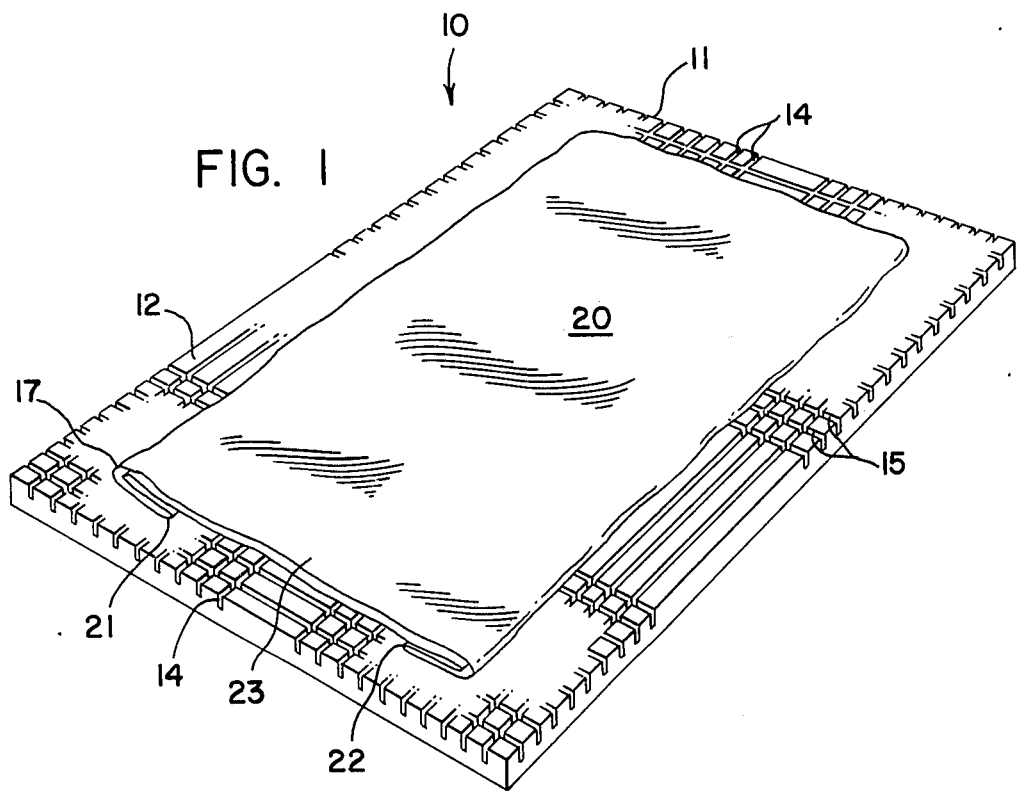
FIG. 1 is a perspective of the base and container means employed in an exemplary device which embodies the concept of the present invention and which is capable of performing the method thereof, the figure specifically depicting the container means as it is preliminarily folded, and received, on the base of an exemplary device.

Referring to the drawings a template forming device embodying the concept of the present invention, and capable of operating in accordance with the method thereof, is identified generally by the numeral 10. The template forming device 10 employs a base 11 having a preferably planar, upper surface 12 within which a plurality of orthogonally disposed grooves, or slots, are recessed. As such, there are longitudinally extending grooves, or slots, 14 which intersect with laterally extending grooves, or slots, 15. It has been found that neither the spacing nor dimension of the grooves 14 and 15 are absolutely critical, but for convenience both the longitudinally and laterally extending grooves (14 and 15, respectively) should be incrementally spaced and be of the same dimensions to effect their hereinafter more fully described function.

In order to permit the desired customization for virtually any patient it has been found that the grooves should be incrementally spaced at no more than about 2 to 2½ inches (5.08 to 6.35 cm). Conversely, the grooves should not be so close together as to degrade, or otherwise weaken, the material from which the base is made. By way of example, if the base were made of a wooden material, such as plywood, which works quite well, the successive grooves should not be incrementally spaced at much less than about ¾ to one inch (1.9 to 2.54 cm).

A plurality of slat means 18 are provided to be insertably receivable within the grooves 14 and 15. The slat means 18 may be provided in a plurality of lengths, but should be closely received when inserted in any selective groove 14 or 15, and the grooves should be of sufficient depth that the slat means 18 will be sufficiently stable, when inserted therein, to effect their function.

Again, but only by way of example, if the slats 18 would also be made of a wooden material they could be approximately ¼ inch (0.635 cm) in thickness and would have a width of approximately 4 inches (10.16 cm). At these dimensions each slat 18 should be insertably received within the grooves 14 or 15 approximately ⅜ inch (0.952 cm) in order to provide the desired stability. Experience has revealed that such slats 18 may most desirably be provided in lengths varying from about three inches (7.62 cm) to about 20 inches (50.8 cm). To employ such slats 18, the grooves 14 and 15 in base 11 would have to have the corresponding dimensions of approximately ¼ inches (0.635 cm) in width and approximately ⅜ inch (0.952 cm) in depth.

It should be appreciated that other materials, however, might provide perfectly acceptable results with quite different dimensions. Hence, it is reiterated that the material and dimensions herein set forth are solely by way of example for a representative apparatus and are not to be construed as a limitation on the invention.

A container means 20 is employed to receive a homogeneous foam mix and overlie the upper surface 12 of the base 11. The container means 20 must be tear-resistant, flexible and must not react with the selected foam mixture. A suitable container means, therefore, may be fabricated from a pliable, sturdy material such as polyvinyl chloride (PVC).

Even though PVC has proven to be a perfectly acceptable material, it should be appreciated that the wall thickness of the bag should be no less than approximately 1.5 mils. Hence, some standard refuse bags, even though made of PVC, cannot be used because their wall thickness is too thin. Some industrial refuse bags, and certain brands of those home refuse bags advertised as having "double wall" thickness, or the like, as well as certain brands of waste compactor bags, however, do possess the requisite wall thickness, and they may be employed.

This minimal wall thickness is required to accomplish two objectives. First, a wall thickness of less than 1.5 mils is too subject to tearing or rupturing. The container means 20 must provide a controlled confinement for the foam mix, if the invention is to be satisfactorily employed, and the objective cannot be achieved if the container means 20 ruptures, or tears. Second, a wall thickness of less than 1.5 mils is too susceptible to wrinkling and could cause an undesirable fold where it might not be visually detectable. Such unobserved folds can capture the foam mixture before it fully foams to create localized "hot spots" that could make the patient uncomfortable, at the leasta, or, at the worst, burn the patient. Such localized hot spots have been observed to melt the PVC bag at, and around, such a fold. Employing a PVC bag having sufficient wall thickness, however, has been found to obviate this potential problem.

A bag measuring approximately 30 by 36 inches (76.2 by 91.44 cm) provides a convenient size that can be readily adapted to virtually any situation, as will become more apparent from the hereinafter described exemplary usage.

Homogeneous foam mixtures that are suitable for practice of the subject invention are not in themselves particularly unique and may include the polyurethane family. Various formulations of the polyurethane family are employed to provide foams having widely disparate, ultimate characteristics. For example, some formulations provide foam that is hydrophilic and are, therefore, eminently suited to be used as supports for floral displays. Other formulations provide foam that possesses antipodal characteristics, and which are, therefore, eminently suited to be used in, or as, flotation devices.

The basic reaction is that of mixing a polyol and a polyisocyanate such as follows:

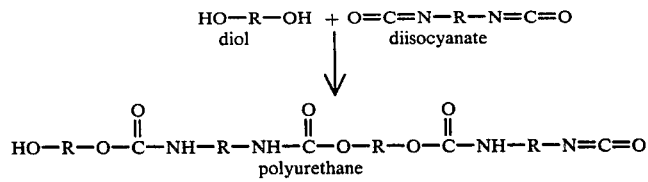

Surfactants, catalysts and blowing agents are generally added in various amounts selectively to provide the desired properties from the wide range available, including such characteristics as hydrophilia, rate of rise, rate of cure, amount of heat release, cell size and rigidity. The preferred polyisocyanate for practice of the subject invention is polymethylenepolyvinyl isocyanate, whereas the preferred polyol is a mixture of various polyols such as ethylene glycol, glycerin, 2,2 dimethyl-1,3-butanediol, 1,2,4 butanetriol, 1,2,6 hexanetriol and the like.

A typical application of the present invention to mold a template for any selected portion of a patient's anatomy would employ the addition of approximately 100 ml to 350 ml of the polyol to 75 ml to 240 ml of the polyisocyanate.

A full appreciation as to the use of the present invention can be conveyed by describing an exemplary usage thereof in combination with appropriate references to the drawings.

The base 11 is suitably positioned such that the portion of the patient's anatomy to be molded thereby can comfortably repose thereon. In the example about to be described the upper torso, neck and head of the patient is to be positioned on the upper, planar surface 12 of the base 11.

As best seen in FIG. 4, the flexible container means 20 in the form of the exemplary PVC bag is placed flat upon the upper surface 12 of the base 11, and the lateral edges 21 and 22 forming the sides of the container means 20 are folded, as at 17, under the main portion 23 thereof such that the upwardly exposed surface of the main portion is an inch or two (2.54 cm to 5.05 cm) wider than the widest portion of the particular patient's anatomy for which a template is to be molded.

The chemicals required to form the foam are then mixed together. Typically the polyisocyanate is provided in a bottle 24 larger than that required, and bottle in which the polyol is provided is emptied into the bottle 24 containing the polyisocyanate. The bottle 24, which now contains the mixed polyisocyanate and polyol is then capped and vigorously shaken for approximately 35 seconds. Thereafter, the bottle 24 is opened and, as best seen in FIG. 4, the contents are poured into container 20 through its open end 26. The bag 20 is held open for approximately 15 seconds, and the open end 26 is then folded under the main portion 23, as at 28 in FIG. 5, effectively to close the bag.

By manipulating the upper wall 29 of the main portion 23 with the hands, also as depicted in FIG. 5, the mixed chemicals are spread evenly within the main portion 23 of the container means 20. Any and all wrinkles are smoothed out of the upper wall 29, and the portion of the patient's anatomy to be molded is then placed in the desired treatment position on the container means 20.

As the foam begins to rise, the sides of the bag 20, at the folds between the sides 21, 22 and the main portion 23, are lifted off the upper surface 12 of the base 11 and pressed into conforming disposition with the adjacent sides of the patient. The slats 18 are then inserted into the approximate longitudinal and lateral grooves 14 and 15, respectively, to hold the raised sides of the container 20 against the adjacent portion of the patient.

With respect to the exemplary use depicted in the drawings, a slat 18A is inserted in groove 15A to maintain the container 20 in contiguous juxtaposition with the top 30 of the patient's head 31. It should be appreciated that thick-sectioned walls of foam are neither required nor desired in the vertically oriented walls of the molded template that surround that portion of the anatomy to be repositioned. If possible, in fact, the thickness of such mold walls should not be permitted to exceed one inch (2.54 cm).

A pair of laterally spaced slats 18B and 18C are inserted in appropriate longitudinal grooves 14A and 14B to delineate the lateral extent of the molded template in the head region.

Similarly, a pair of slats 18D and 18E are inserted in appropriate longitudinal grooves 14C and 14D to maintain the container means 20 against the patient's left shoulder 32 and left arm 33 as the template is being formed.

Figure 2:
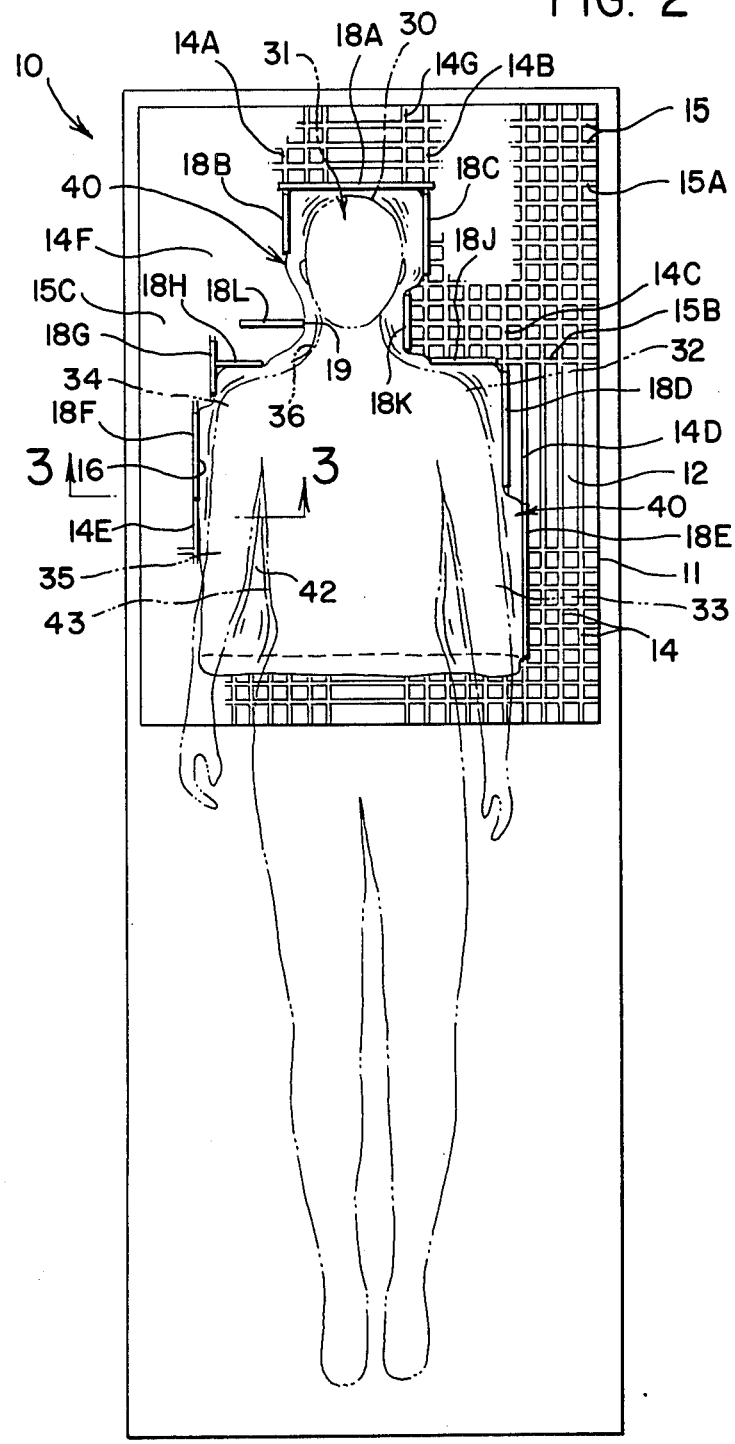
FIG. 2 is a top plan view of the exemplary device, a portion of which is represented in FIG. 1 and depicting a human patient disposed so that the device will form a template of the upper torso, neck and head.

The position of the slats to form the template around the right shoulder 34 and arm 35 may mirror the disposition of the slats 18D and 18E employed to form the template around the left shoulder 32 and arm 33, but it must be understood that no particular arrangement is critical. For example, as depicted in FIG. 2, a slat 18F may be received in groove 14E to maintain the container means 20 against the upper right arm 35, and slat 18G may be received within groove 14F to retain the container means 20 against the right shoulder 34.

Similarly, one convenient approach may be to position slats 18H and 18J within the lateral groove 15B to mold the template against the tops of the respective shoulders 34 and 32. Slat 18K may likewise be received within groove 14G to restrain the container means 20 against the left side of the neck 36.

The slats 18A through 18K are all depicted as being positioned so that the lateral surface 16 on each engages the flexible container means 20. However, the slats 18 can also be employed so that the ends, or edge, 19 provides the restraining contact against the flexible container means 20. For example, in the neck region 36, as depicted in FIG. 2, slat 18L may be inserted in the appropriate lateral grooves 15C such that the edge 19 serves to restrain the container means 20 and force the foam to rise, or expand, toward the patient. Judicious placement of the slats 18 during the foaming process, as will be acquired by experience, will permit an extremely accurate and close-fitting template 40 to be achieved.

Figure 3:
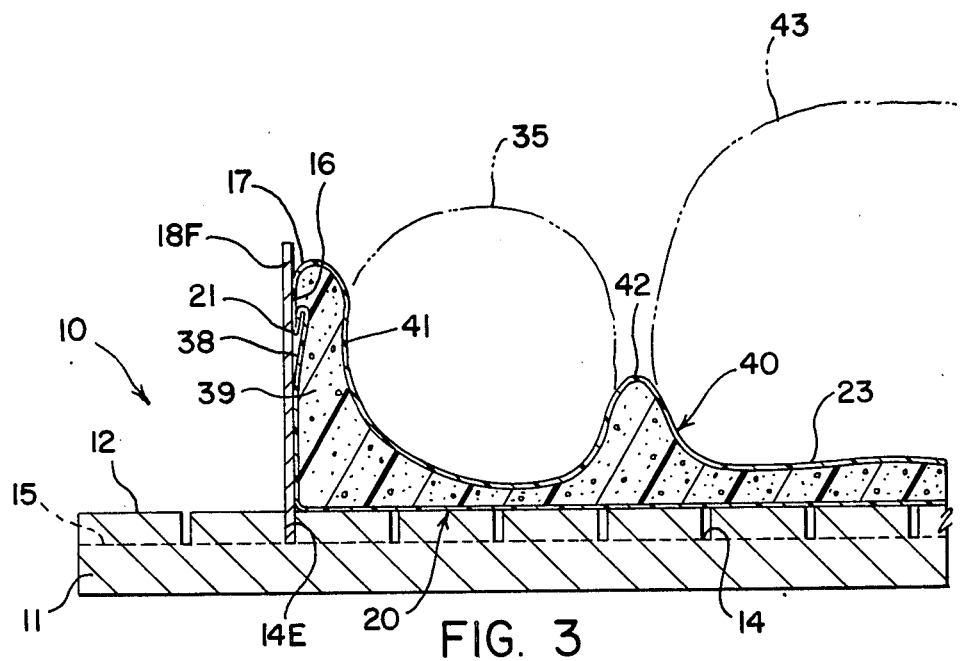
FIG. 3 is an enlarged, fragmentary cross-section taken substantially along line 3—3 of FIG. 2, said FIG. 3 appearing on the same sheet of drawings as FIG. 1.

FIG. 3 specifically demonstrates the lateral shoulder restraint formed by slat 18F residing in groove 14E, in which position its lateral surface 16 is securely pressed against the outer wall 38 of the flexible container 20 to press the foam 39 toward the patient and thereby bias the inner wall 41 into the desired contact with the patient. This procedure is repeated around the periphery of that portion of the patient's anatomy to be molded with care being taken to insure that the patient remains as still as possible during the procedure. It should be appreciated that the innate flexibility of the container means 20 permits the foam 39 to force the upper surface 23 thereof into a ridge 42 which extends into the natural space between the right arm 35 and the body 43 of the patient.

Folding the lateral edges 21 and 22 of the container means 20, as depicted as 17 in FIGS. 1 and 4, to present an upwardly exposed surface for the main portion 23 that is slightly wider than the width of the patient's anatomy to be molded generally provides an inner wall 41 which will extend upward a sufficient extent to provide the desired height for the lateral walls 44 of the template 40 so the template can be repeatedly employed effectively to reposition the patient. However, in some situations it may be necessary, or desirable, for the lateral walls 44 more fully to embrace the patient. In fact, in some situations it may be desirable for the inner wall 41 thereof to extend both upwardly and inwardly to assure the desired support for the patient. This result can be effectively achieved by carefully extending the folds 17. This eversion of the folds 17, as depicted in FIG. 7, provides a facile means for customizing the extent to which the lateral walls 44 of the template 40 embrace the patient's anatomy. If desired, of course, the closed end 45 of the container means 20 may be similarly be folded in order to provide the same customization option along the top edge 46 (FIG. 5) as has heretofor been described with respect to the lateral edges.

The foaming action should subside after about fifteen minutes, and thereafter the patient can be carefully extricated from the newly formed template 40. The template 40 is then allowed to harden for the required five to ten minutes on a separate flat surface.

The finished template can repeatedly be used for successive treatment of the particular patient and can even be tailored to the type of treatment desired, as, for example, by cutting access holes directly through the template 40.

It should be apparent that the invention accomplishes the objects thereof. As stated, a variety of boards, receptacles, restraints, homogeneous foam mixtures and methods of securing the restraints can be employed in the practice of this invention. It is to be understood that such variations are intended to fall within the scope of the claimed invention and that the subject invention is not to be limited by the specific method of operation described and/or depicted by the drawings nor is the invention to be limited by the specific chemical and mechanical components identified and described herein. These have been designated merely to provide a demonstration of operability and the selection of mechanically equivalent arrangements is not deemed a departure from the spirit of the invention herein disclosed and described; the scope of the invention being limited solely by the scope of the attached claims.

I claim:

1. A method of molding a template for repositioning a portion of human anatomy comprising the steps of:

providing a base means to which a plurality of slat means can be secured in selected positions;

positioning a flexible container means upon said base means;

introducing a homogeneous foam mixture into said flexible container means;

positioning a selected portion of human anatomy on said flexible container means and allowing said homogeneous foam mixture to rise around said portion of the human anatomy;

placing, simultaneously with further rising of said foaming mixture, a plurality of slat means against said flexible container means containing said foam mixture to direct said foam mixture around said portion of the human anatomy; and waiting a sufficient length of time for said homogeneous foam mixture to set and form a template for said portion of the human anatomy.

2. A method, as set forth in claim 1, wherein said homogeneous foam mixture is produced by mixing the contents of a first container means containing a polyol mixture to the contents of a second container means containing polyisocynanate.

3. A method, as set forth in claim 2, wherein the amount of said polyol mixture is from about 100 ml to 350 ml and the amount of polyisocyanate is from about 75 ml to 240 ml.

4. A method, as set forth in claim 1, wherein said homogeneous foam mixture is a polyurethane foam.

5. A method, as set forth in claim 1, wherein said step of positioning said flexible container means comprises the additional steps of:

determining a widest area of the patient's anatomy for which a template is to be molded; and, folding said flexible container means to match said widest area.

6. A method, as set forth in claim 5, comprising the additional steps of:

folding the container means after the homogeneous foam mixture is introduced to close the container means and thereby simultaneously also match the length of the container to the longest longitudinal dimension to be molded.

7. A method, as set forth in claim 5, comprising the additional step of:

everting the folds of the container means to direct said foam mixture further upwardly and inwardly against the desired portion of the human anatomy for which a template is to be molded.

8. A method, as set forth in claim 6, comprising the additional step of:
folding the end of the container means opposite to the end through which the foam mixture is introduced.

9. A method, as set forth in claim 8, comprising the additional step of:
everting selected folds of the container means to direct said foam mixture further upwardly and inwardly against the desired portion of the human anatomy for which a template is to be molded.

10. A device for molding a template by which to reposition a portion of the human anatomy comprising:
base means;
a plurality of laterally spaced, orthogonal grooves in said base means;
a plurality of slat means insertably receivable in selected of said grooves; and,
a flexible container means receivable on a portion of said base.

11. A device, as set forth in claim 10, in which a homogeneous foam mixture is received within said flexible container means.

12. A device, as set forth in claim 11, in which a patient is positioned, as desired, on said flexible container means in which the homogeneous foam mixture is received, said slat means being insertably received in selective slots to direct and maintain the foam in said flexible container means to form a template about at least a selected portion of said patient.

* * * * *